United States Patent
Melkent et al.

(10) Patent No.: US 8,211,178 B2
(45) Date of Patent: Jul. 3, 2012

(54) INTERVERTEBRAL IMPLANT WITH A PIVOTING END CAP

(75) Inventors: Anthony J. Melkent, Memphis, TN (US); Eric A. Potts, Indianapolis, IN (US); Stanley T. Palmatier, Olive Branch, MS (US)

(73) Assignee: Warsaw Orthopedic, Warsaw, IN (US)

(*) Notice: Subject to any disclaimer, the term of this patent is extended or adjusted under 35 U.S.C. 154(b) by 374 days.

(21) Appl. No.: 12/487,189

(22) Filed: Jun. 18, 2009

(65) Prior Publication Data

US 2010/0324687 A1    Dec. 23, 2010

(51) Int. Cl.
*A61F 2/44* (2006.01)
(52) U.S. Cl. .................................................. 623/17.16
(58) Field of Classification Search ..... 623/17.11–17.17
See application file for complete search history.

(56) References Cited

U.S. PATENT DOCUMENTS

| | | | |
|---|---|---|---|
| 4,657,550 A | 4/1987 | Daher | |
| 5,236,460 A * | 8/1993 | Barber | 623/17.15 |
| 5,443,515 A | 8/1995 | Cohen et al. | |
| 5,480,442 A | 1/1996 | Bertagnoli | |
| 5,534,029 A | 7/1996 | Shima | |
| 5,562,738 A | 10/1996 | Boyd et al. | |
| 5,571,192 A | 11/1996 | Schonoffer et al. | |
| 5,702,453 A | 12/1997 | Rabbe et al. | |
| 5,702,455 A | 12/1997 | Saggar | |
| 5,723,013 A | 3/1998 | Jeanson et al. | |
| 5,776,197 A | 7/1998 | Rabbe et al. | |
| 5,776,198 A | 7/1998 | Rabbe et al. | |
| 5,827,328 A | 10/1998 | Buttermann | |
| 5,865,848 A | 2/1999 | Baker | |
| 5,895,428 A | 4/1999 | Berry | |
| 5,899,941 A | 5/1999 | Nishijima et al. | |
| 5,916,267 A | 6/1999 | Tienboon | |
| 5,989,290 A | 11/1999 | Biedermann et al. | |
| 5,989,291 A | 11/1999 | Ralph et al. | |
| 6,015,436 A | 1/2000 | Schonhoffer | |

(Continued)

FOREIGN PATENT DOCUMENTS

WO    9617564    6/1996

(Continued)

OTHER PUBLICATIONS

US 5,401,265, 03/1995, Buttner-Janz et al. (withdrawn)

*Primary Examiner* — Eduardo C Robert
*Assistant Examiner* — James Palmer

(57) ABSTRACT

Implants sized to be inserted into an intervertebral space between first and second vertebral members. The implants may include a body with opposing first and second ends. An end cap may be connected to the body and include a first side with a contact surface that faces away from the body and is configured to contact against one of the first and second vertebral members when the implant is positioned in the intervertebral space. The end cap may also include a second side that faces towards the body. A connection mechanism may connect the end cap and the body for the end cap to pivot to adjust an angular position of the end cap relative to the body. The body and the end cap may each include locking features that engage together to lock an angular position of the end cap. The locking features may be configured to overlap at each of the angular positions to engage together and maintain the angular position of the end cap relative to the body when the implant is positioned in the intervertebral space.

17 Claims, 16 Drawing Sheets

U.S. PATENT DOCUMENTS

| | | | |
|---|---|---|---|
| 6,019,792 | A | 2/2000 | Cauthen |
| 6,039,761 | A * | 3/2000 | Li et al. ................ 623/17.16 |
| 6,045,579 | A | 4/2000 | Hochshuler et al. |
| 6,156,067 | A | 12/2000 | Bryan et al. |
| 6,159,244 | A | 12/2000 | Suddaby |
| 6,174,334 | B1 | 1/2001 | Suddaby |
| 6,176,881 | B1 | 1/2001 | Schar et al. |
| 6,190,413 | B1 | 2/2001 | Sutcliffe |
| 6,190,414 | B1 * | 2/2001 | Young et al. ............. 623/17.15 |
| 6,200,348 | B1 | 3/2001 | Biedermann et al. |
| 6,296,665 | B1 | 10/2001 | Strnad et al. |
| 6,299,642 | B1 | 10/2001 | Chan |
| 6,332,895 | B1 | 12/2001 | Suddaby |
| 6,368,350 | B1 | 4/2002 | Erickson et al. |
| 6,375,681 | B1 | 4/2002 | Truscott |
| 6,395,034 | B1 | 5/2002 | Suddaby |
| 6,436,142 | B1 | 8/2002 | Pacs et al. |
| 6,520,991 | B2 * | 2/2003 | Huene ..................... 623/17.11 |
| 6,524,341 | B2 | 2/2003 | Lang et al. |
| 6,562,074 | B2 | 5/2003 | Gerbec et al. |
| 6,610,090 | B1 | 8/2003 | Boham et al. |
| 6,616,695 | B1 | 9/2003 | Crozet et al. |
| 6,648,917 | B2 | 11/2003 | Gerbec et al. |
| 6,652,584 | B2 | 11/2003 | Michelson |
| 6,682,562 | B2 | 1/2004 | Viart et al. |
| 6,685,742 | B1 | 2/2004 | Jackson |
| 6,709,458 | B2 | 3/2004 | Michelson |
| 6,716,247 | B2 | 4/2004 | Michelson |
| 6,723,126 | B1 | 4/2004 | Berry |
| 6,730,088 | B2 * | 5/2004 | Yeh ............................. 606/247 |
| 6,793,679 | B2 | 9/2004 | Michelson |
| 6,808,538 | B2 | 10/2004 | Paponneau |
| 6,814,756 | B1 | 11/2004 | Michelson |
| 6,821,298 | B1 | 11/2004 | Jackson |
| 6,835,206 | B2 | 12/2004 | Jackson |
| 6,849,093 | B2 | 2/2005 | Michelson |
| 6,866,682 | B1 | 3/2005 | An et al. |
| 6,893,464 | B2 | 5/2005 | Kiester |
| 6,902,579 | B2 | 6/2005 | Harms et al. |
| 6,905,512 | B2 | 6/2005 | Paes et al. |
| 6,908,485 | B2 | 6/2005 | Crozet et al. |
| 6,953,477 | B2 | 10/2005 | Berry |
| 6,955,691 | B2 | 10/2005 | Chae et al. |
| 6,962,606 | B2 | 11/2005 | Michelson |
| 6,972,035 | B2 | 12/2005 | Michelson |
| 7,008,453 | B1 | 3/2006 | Michelson |
| 7,022,138 | B2 | 4/2006 | Mashburn |
| 7,044,971 | B2 | 5/2006 | Suddaby |
| 7,056,343 | B2 | 6/2006 | Schafer et al. |
| 7,094,257 | B2 | 8/2006 | Mujwid et al. |
| 7,214,243 | B2 | 5/2007 | Taylor |
| 7,331,995 | B2 | 2/2008 | Eisermann et al. |
| 7,419,505 | B2 | 9/2008 | Fleischmann et al. |
| 7,485,146 | B1 * | 2/2009 | Crook et al. ................ 623/17.15 |
| 2003/0050701 | A1 | 3/2003 | Michelson |
| 2004/0049271 | A1 | 3/2004 | Biedermann et al. |
| 2004/0102848 | A1 | 5/2004 | Michelson |
| 2004/0153160 | A1 | 8/2004 | Carrasco |
| 2004/0167626 | A1 | 8/2004 | Geremakid et al. |
| 2004/0186569 | A1 | 9/2004 | Berry |
| 2004/0249461 | A1 | 12/2004 | Ferree |
| 2004/0254643 | A1 | 12/2004 | Jackson |
| 2005/0004673 | A1 | 1/2005 | Kluger |
| 2005/0010294 | A1 | 1/2005 | Michelson |
| 2005/0015149 | A1 | 1/2005 | Michelson |
| 2005/0021041 | A1 | 1/2005 | Michelson |
| 2005/0085910 | A1 | 4/2005 | Sweeney |
| 2005/0096744 | A1 | 5/2005 | Trieu et al. |
| 2005/0113916 | A1 | 5/2005 | Branch, Jr. |
| 2005/0113921 | A1 | 5/2005 | An et al. |
| 2005/0113924 | A1 | 5/2005 | Buttermann |
| 2005/0187634 | A1 | 8/2005 | Berry |
| 2005/0209697 | A1 | 9/2005 | Paponneau et al. |
| 2005/0234550 | A1 | 10/2005 | Metz-Stavenhagen |
| 2006/0004447 | A1 | 1/2006 | Mastririo et al. |
| 2006/0058878 | A1 | 3/2006 | Michelson |
| 2006/0069439 | A1 | 3/2006 | Zychermann et al. |
| 2006/0074490 | A1 | 4/2006 | Sweeney |
| 2006/0079962 | A1 | 4/2006 | Michelson |
| 2006/0100710 | A1 | 5/2006 | Gutlin et al. |
| 2007/0162133 | A1 | 7/2007 | Doubler et al. |
| 2007/0191954 | A1 * | 8/2007 | Hansell et al. ............. 623/17.15 |
| 2008/0114467 | A1 | 5/2008 | Capote et al. |
| 2008/0161922 | A1 | 7/2008 | Rhoda |
| 2008/0243254 | A1 * | 10/2008 | Butler ....................... 623/17.16 |
| 2010/0094424 | A1 * | 4/2010 | Woodburn et al. ......... 623/17.16 |

FOREIGN PATENT DOCUMENTS

| | | |
|---|---|---|
| WO | 9963913 | 12/1999 |
| WO | 2004100837 | 11/2004 |
| WO | 2005055887 | 6/2005 |

\* cited by examiner

INTERVERTEBRAL IMPLANT WITH A PIVOTING END CAP

BACKGROUND

The present application is directed to devices and methods for stabilizing vertebral members, and more particularly, to intervertebral implants and methods of use for replacing an intervertebral disc, vertebral member, or combination of both to distract and/or stabilize the spine.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions may lead to damage of the intervertebral discs and/or the vertebral members. The damage may result from a variety of causes including but not limited to a specific event such as trauma, a degenerative condition, a tumor, or infection. Damage to the intervertebral discs and vertebral members can lead to pain, neurological deficit, and/or loss of motion.

Various procedures include replacing the entirety or a section of a vertebral member, the entirety or a section of an intervertebral disc, or both. One or more replacement implants may be inserted to replace the damaged vertebral members and/or discs. The implants are configured to be inserted into the intervertebral space and contact against the remaining adjacent vertebral members. The implants reduce or eliminate the pain and neurological deficit, and increase the range of motion.

The curvature of the spine and general shapes of the vertebral members may make it difficult for the implants to adequately contact the adjacent vertebral members. There is a need for implants configurable to match the spinal anatomy for secure contact when implanted into an intervertebral space.

SUMMARY

The present application is implants for insertion into an intervertebral space between first and second vertebral members. The implants may include a body with opposing first and second ends. An end cap may be connected to the body and include a first side with a contact surface that faces away from the body and is configured to contact against one of the first and second vertebral members when the implant is positioned in the intervertebral space. The end cap may also include a second side that faces towards the body. A connection mechanism may connect the end cap and the body for the end cap to pivot to adjust an angular position of the end cap relative to the body. The body and the end cap may each include locking features that engage together to lock an angular position of the end cap. The locking features may be configured to overlap at each of the angular positions to engage together and maintain the angular position of the end cap relative to the body when the implant is positioned in the intervertebral space. The locking features may include tooth sets that include one or more teeth.

The various aspects of the various embodiments may be used alone or in any combination, as is desired.

DETAILED DESCRIPTION

Figure 1:
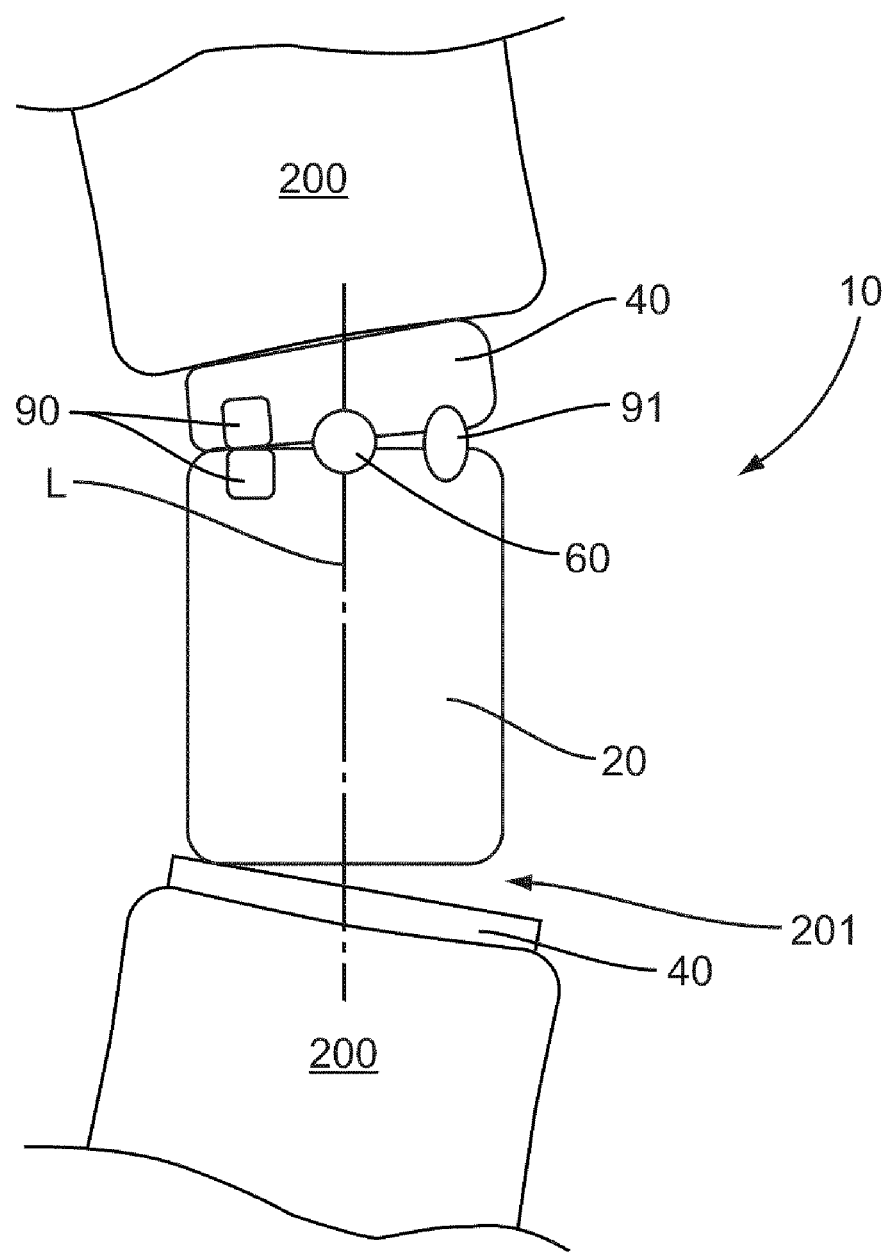
FIG. 1 is a side view of an implant positioned between vertebral members according to one embodiment.

The present application is directed to intervertebral implants for spacing apart vertebral members. FIG. 1 illustrates an implant 10 positioned within an intervertebral space 201 formed between vertebral members 200. The implant 10 includes a body 20 and an end cap 40. One or more connectors 60 pivotally connect the end cap 40 to adjust an angle that the end caps 40 are positioned relative to the body 20 to improve contact with the vertebral members 200 and/or drive angular correction of the spine. Locking features 90 are positioned in an overlapping arrangement on the end cap 40 and body 20 to engage together at the desired angular position to lock the end cap 40 relative to the body 20. One or more biasing members 91 may axially position the end cap 40 along a longitudinal axis L relative to the body 20. The implant 10 may also include a second end cap 40 positioned at the opposite end. The second end cap 40 may be the same or different than the first end cap.

Figure 2:
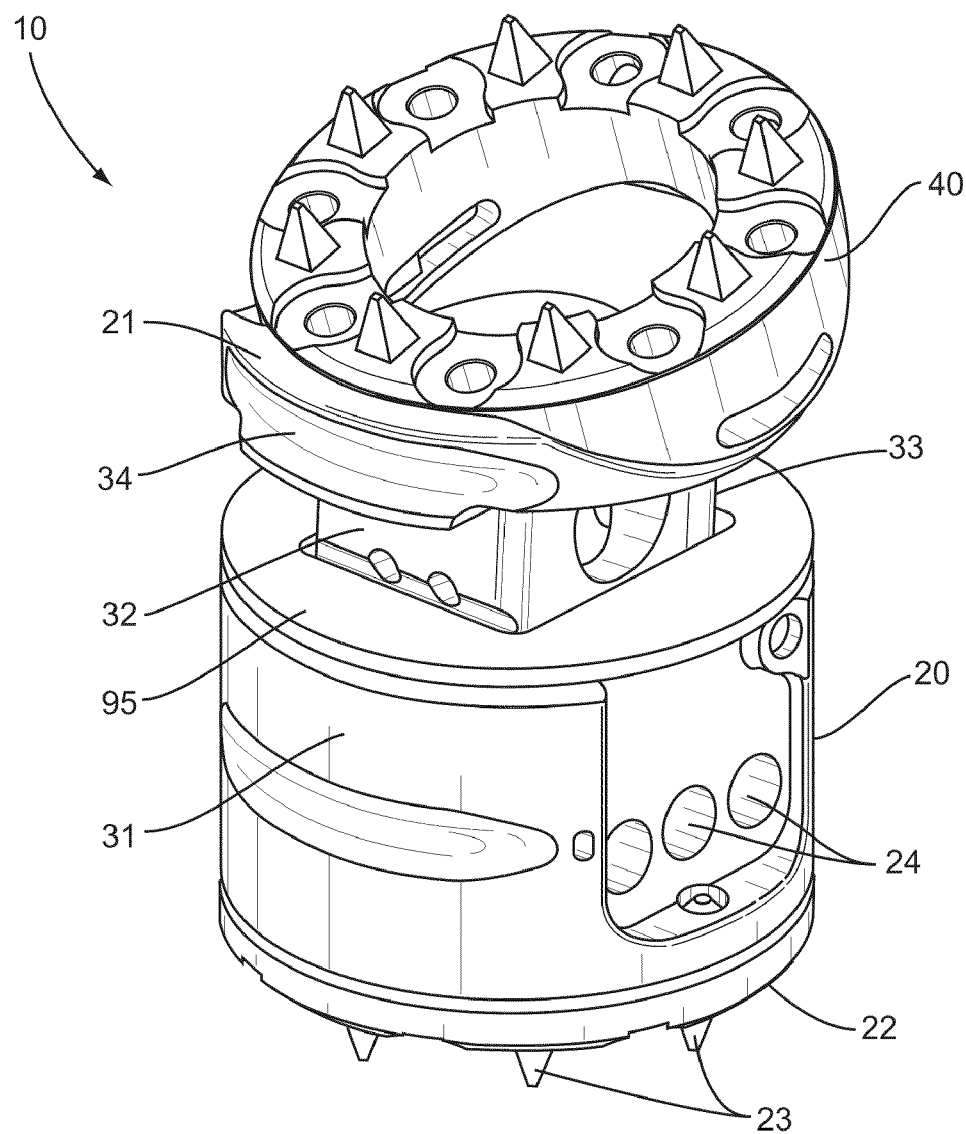
FIG. 2 is a perspective view of an implant according to one embodiment.
Figure 3:
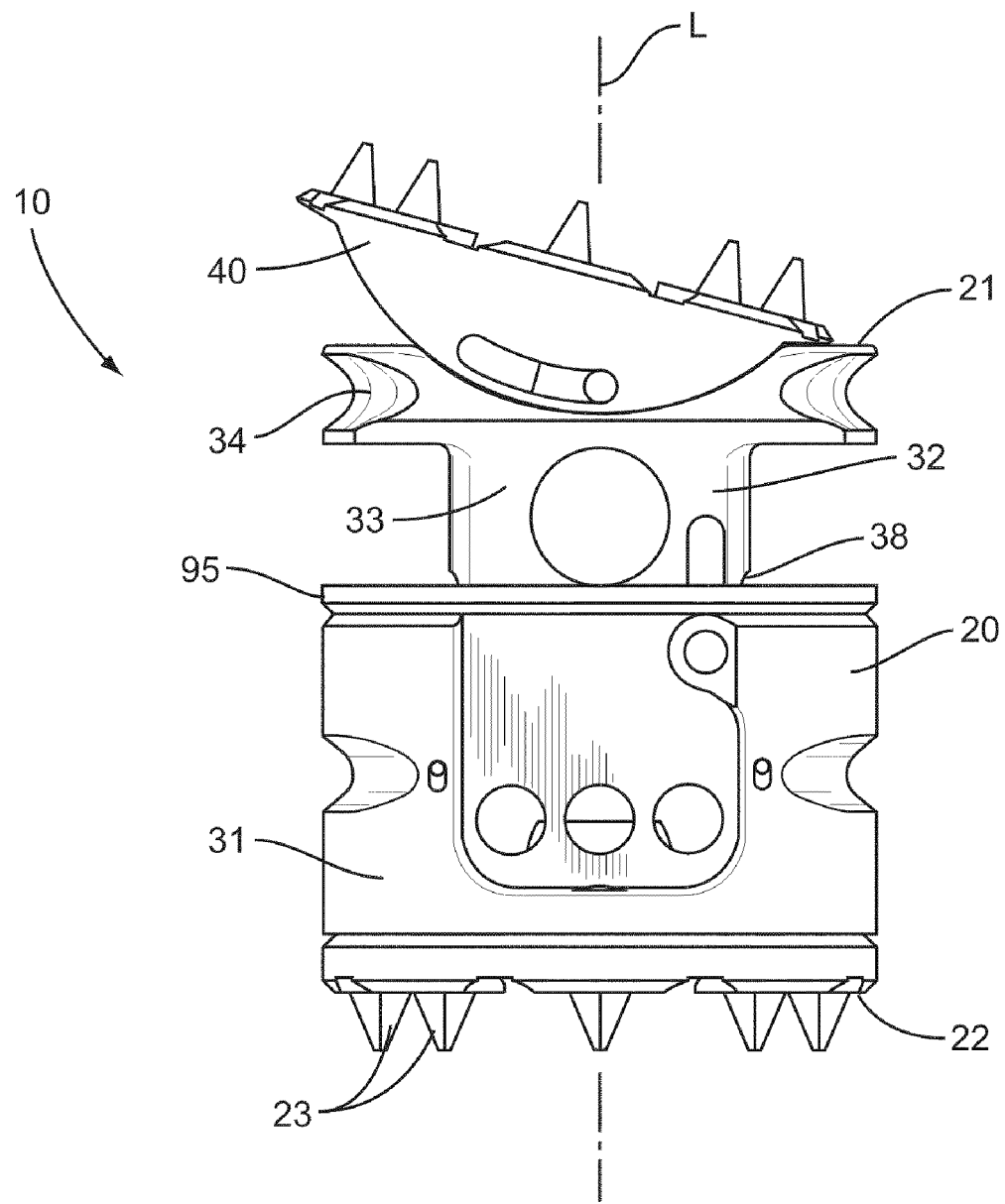
FIG. 3 is a side view of an implant according to one embodiment.

FIGS. 2 and 3 illustrate an implant 10 with a body 20 and end cap 40. The body 20 in combination with the end cap 40 is sized to fit within the intervertebral space 201 and includes a first end 21 and a second end 22. The second end 22 may include teeth 23 that engage with one of the vertebral members 200. The body 20 may include an elongated shape with a longitudinal axis L, and may include a hollow interior sized to receive bone growth material. One or more apertures 24 may extend through the body 20 to the hollow interior.

The body 20 may be constructed from a single section with a fixed height measured between the first and second ends 21, 22. Body 20 may also be constructed of two or more relatively movable sections to adjust the height. FIGS. 2 and 3 include the body 20 with a first outer section 31 and a second inner section 32. The outer section 31 includes a hollow interior and the inner section 32 includes a neck 33 and a base 34. The neck 33 is sized to fit within and axially move along the hollow interior to adjust a height of the body 20 defined along the longitudinal axis L. Both the outer and inner sections 31, 32 may be hollow and include one or more apertures to receive bone growth material.

Figure 4:
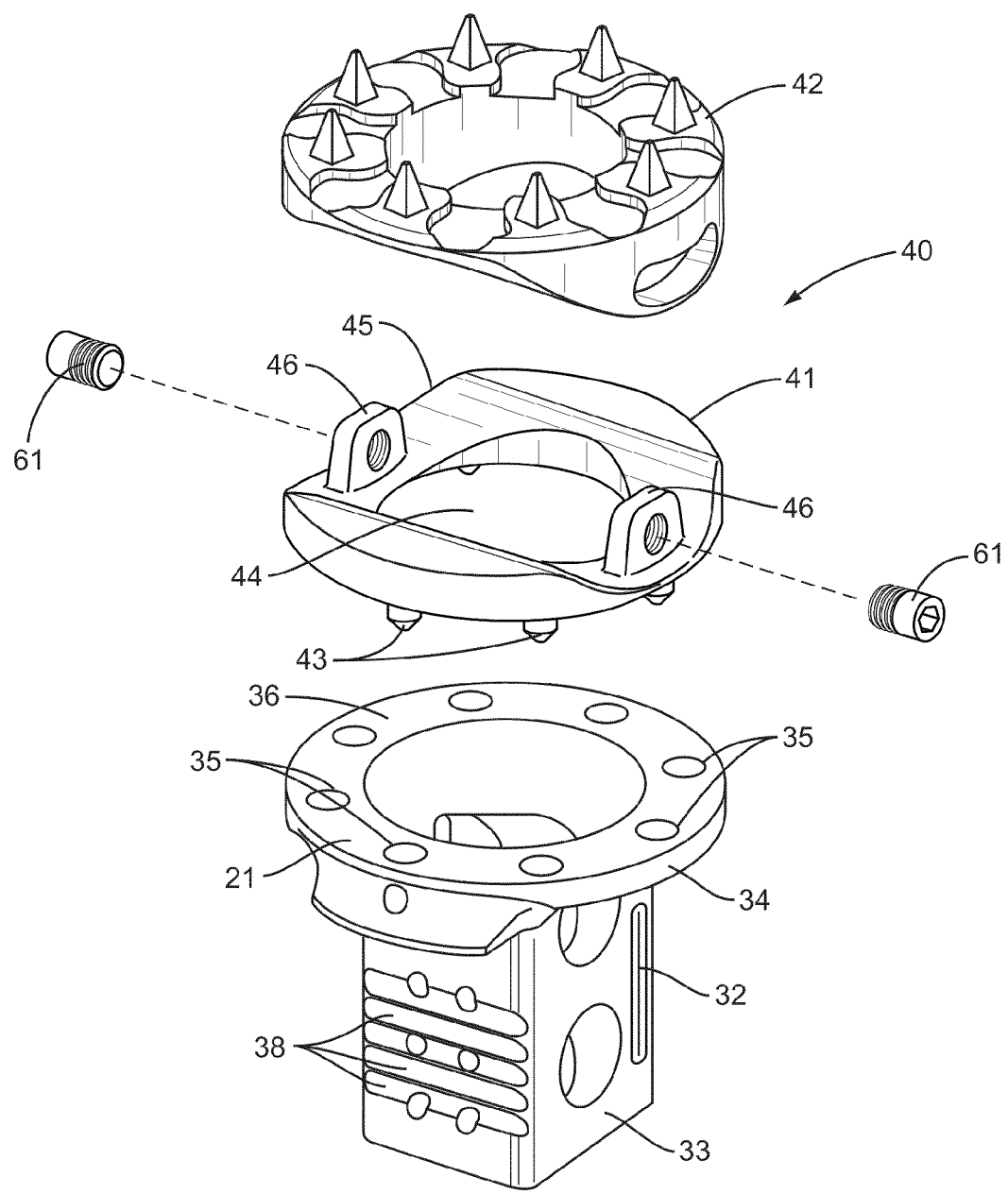
FIG. 4 is an exploded perspective view of an end cap and a section of a body according to one embodiment.
Figure 10:
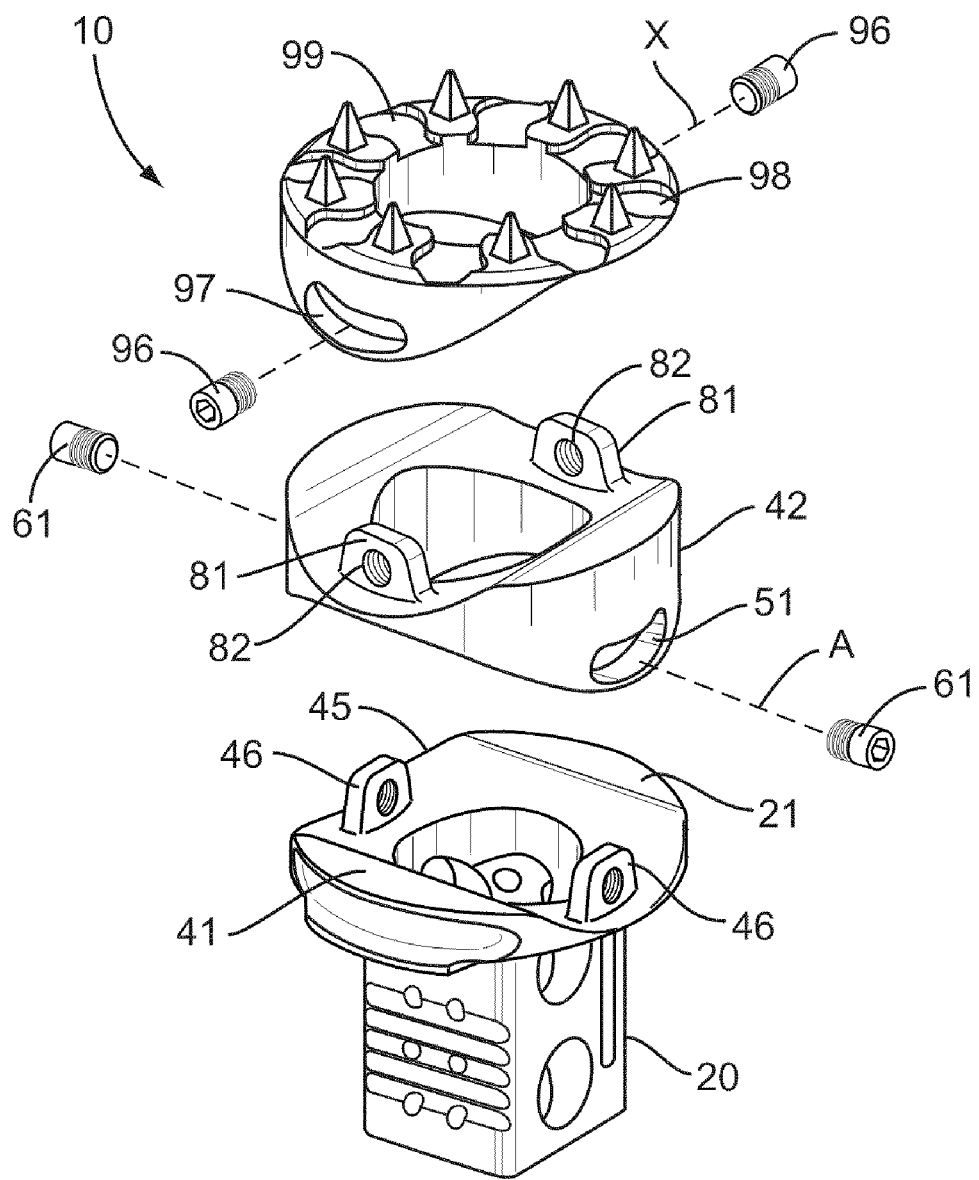
FIG. 10 is an exploded perspective view of an end cap and a section of a body according to one embodiment.
Figure 12:
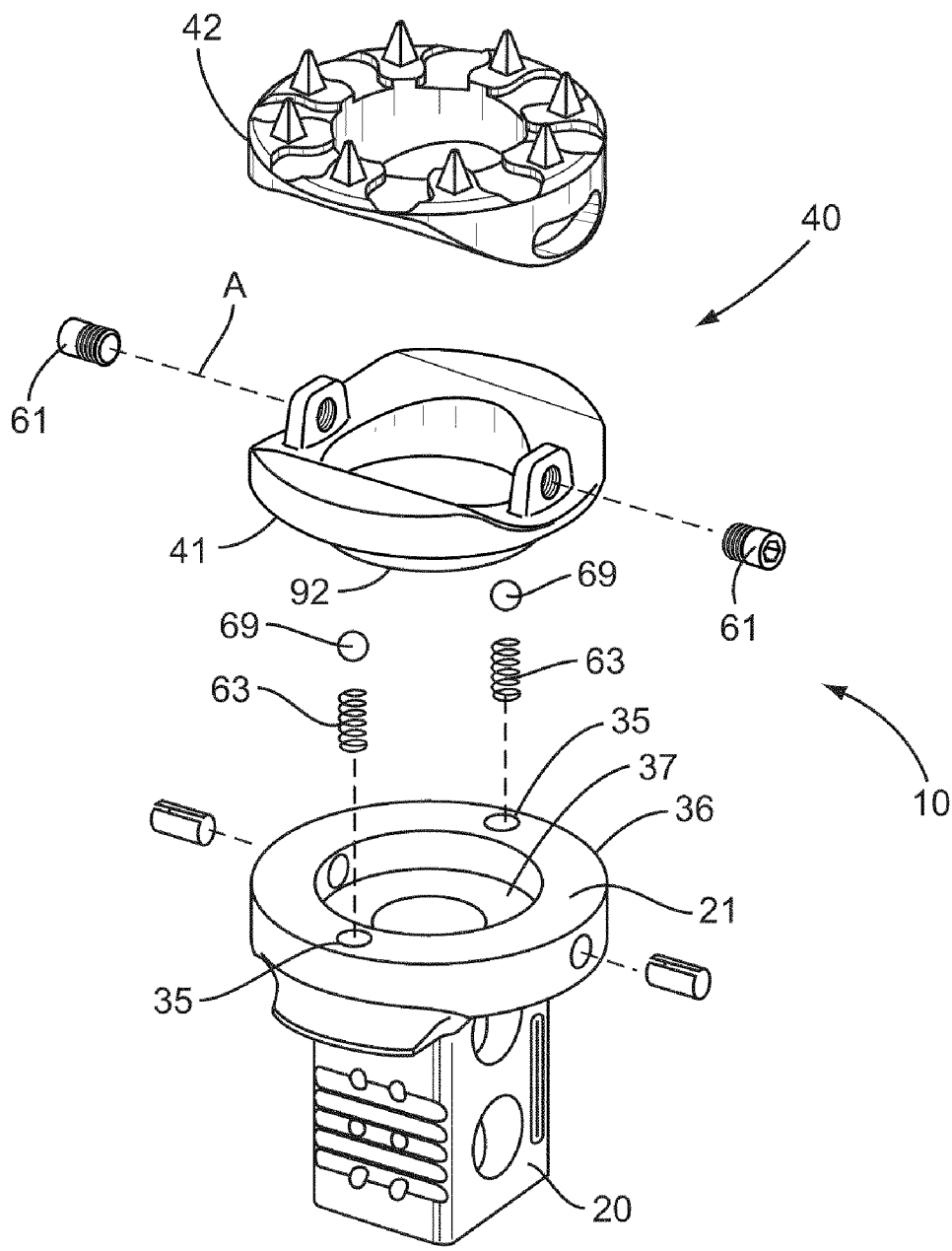
FIG. 12 is an exploded perspective view of an end cap and a section of a body according to one embodiment.

The body 20 is configured to receive the end cap 40. FIG. 4 includes the first end 21 with a support surface 36 that extends around a periphery of the hollow interior space. In this embodiment, the support surface 36 is substantially flat and includes a plurality of apertures 35. The apertures 35 are evenly spaced around the periphery and sized to receive prongs 43 that extend outward from the end cap 40. FIG. 12 includes an embodiment with the first end 21 including a support surface 36 with apertures 35 to receive biasing members 63 and balls 69 to engage with the end cap 40. A shelf 37 is positioned further within the body 20. FIG. 10 includes the first end 21 with a pair of posts 46 and a concave section 45 to receive the end cap 40.

In the body 20 with a two-section configuration as illustrated in FIG. 2, a securing mechanism 95 may secure the sections 31, 32 together to fix the height. In one embodiment, the securing mechanism are configured to receive one or more cylindrical rods (not illustrated) that seat within the plurality of scallops 38 that extend along the neck 33. U.S. Patent Publication No. 2008/0114467, discloses embodiments of an implant that may be used with end caps and include a multiple-section body and a locking mechanism and is herein incorporate by reference in its entirety.

An end cap 40 is positioned at one of the first and second ends 21, 22 of the body 20. The end cap 40 can pivot relative to the body 20 to improve contact against the opposing vertebral member 200 and/or drive or maintain spinal alignment. The end cap 40 may include a single section, or may include multiple sections. FIG. 4 includes an end cap 40 with first and second sections 41, 42. The first section 41 connects to the body (not illustrated in FIG. 4), and the second section 42 connects to the first section 41 and contacts against the vertebral member 200.

Figure 5:
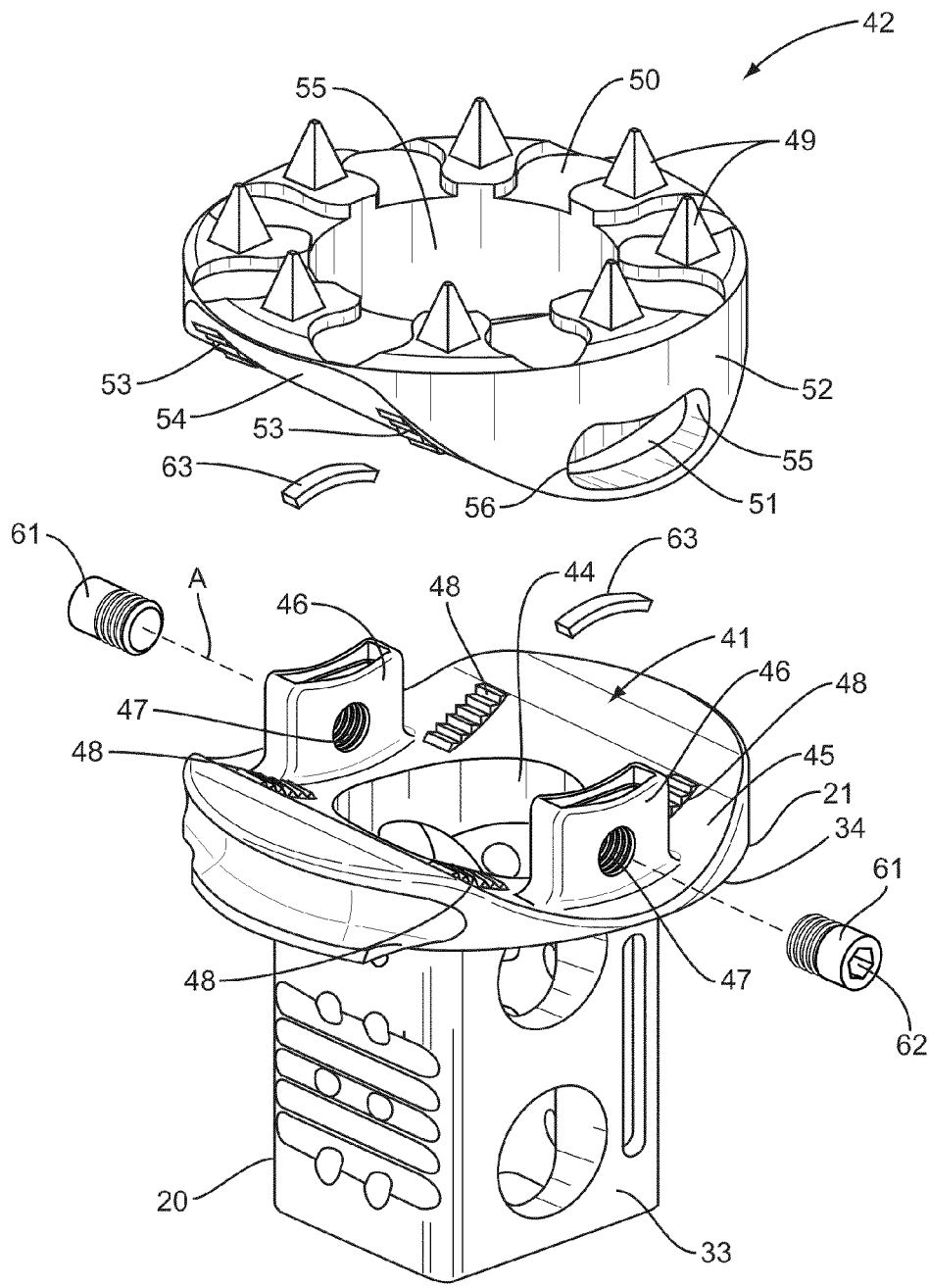
FIG. 5 is an exploded perspective view of an end cap and a section of a body according to one embodiment.

The first section 41 is constructed to connect to the body 20. A plurality of prongs 43 extend outward from an inner side and are positioned around the periphery and sized and positioned to fit within the apertures 35 in the first end 21. The prongs 43 may include tapered ends to facilitate insertion into the apertures 35. The prongs 43 and apertures 35 may be evenly spaced to position the first section 41 at various rotational positions relative to the body 20. FIG. 5 includes the first section 41 after being connected to the body 20. The first section 41 may also be connected to the body 20 by other manners including but not limited to adhesives and mechanical fasteners such as screws, clips, pins, and rings.

FIG. 4 includes the prongs 43 entering the apertures 35 in a longitudinal direction. The prongs 43 and apertures 35 may also be configured to attach in other manners for rotation or sliding of the first section 41 relative to the first end 21. One embodiment includes the prongs 43 extending outward in a direction perpendicular to the longitudinal axis L (see FIG. 1) and configured to fit within one or more slots in the first end 21.

The outer side of the first section 41 is configured to pivotally receive the second section 42. As illustrated in FIGS. 4 and 5, the outer side includes a concave section 45. The concave section 45 may extend across the entirety or a limited portion of the outer side. A pair of posts 46 are positioned within the concave section 45 and positioned on opposing sides of a central aperture 44 that extends through the first section 41. Each post 46 includes an aperture 47 sized to receive a fastener 61. The apertures 47 may each be threaded to engage with threaded fasteners 61. The fasteners 61 may also include a drive feature 62 on the outer end. Drive feature 62 may include a recess shaped to receive a drive tool for connecting the fastener 61 to the post 46. Fasteners 61 may include various shapes and configurations, including but not limited threaded members and press-fit pins.

Teeth 48 are positioned on the outer side to engage with corresponding teeth 53 on the second section 42. FIG. 5 includes four sets of teeth 48 positioned on the concave section 45. Each set of teeth 48 includes a row of multiple teeth. The embodiment of FIG. 5 includes the rows positioned substantially perpendicular to the axis A that extends through the apertures 47 of the posts 46. In one embodiment, the rows extend across the entire concave section 45. One or more of the rows may also extend away from the longitudinal axis A at different angular orientations. Further, each set of teeth 48 may be the same, or may include different shapes and/or sizes of teeth 48, and different numbers of teeth 48. The first section 41 may also be constructed without teeth.

Figure 6:
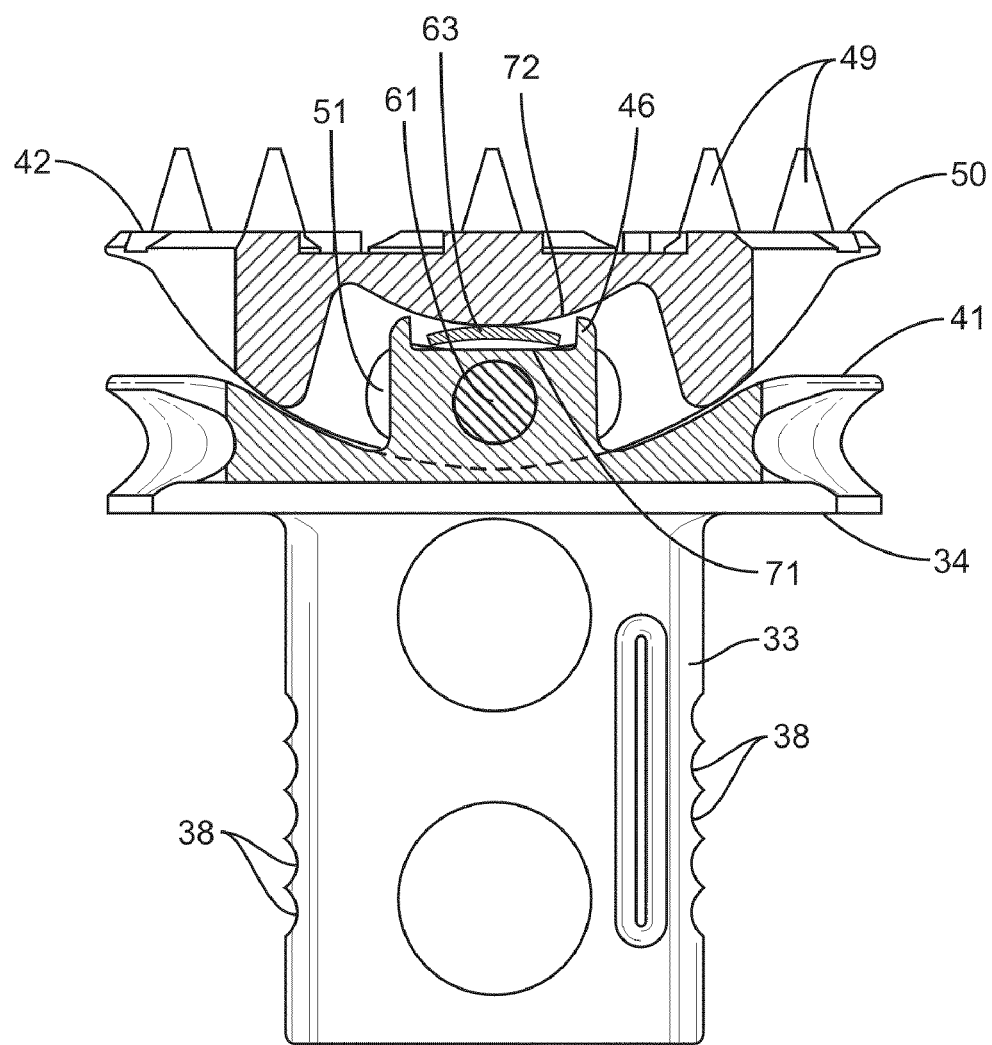
FIG. 6 is a partial sectional view of teeth on an end cap engaging together according to one embodiment.

The second section 42 is pivotally connected to the first section 41. As illustrated in FIGS. 5 and 6, the second section 42 includes an annular shape with a central opening 55. A contact surface 50 extends around the central opening 55 and may include teeth 49 to engage with the vertebral member 200. The number, size, shape, and spacing of the teeth 49 may vary. An inner side includes a convex section 54 sized to complement the concave section 45 of the first section 41. Teeth 53 are positioned on the convex section 54 to engage with the opposing teeth 48 on the concave section 45. The convex section 54 is sized and positioned to locate the teeth 53 in the appropriate location for engagement with the opposing teeth 48.

In one embodiment, teeth 53 are aligned in four rows to correspond to the rows of teeth 48 on the first section 41. The rows of teeth 53 are aligned substantially perpendicular to the axis A and for the teeth 53 to overlap and engage with the opposing teeth 48 at the various angular positions of the second section 42. The teeth 48, 53 themselves may be aligned at various angular positions, such as being substantially parallel with the axis A. The teeth 48, 53 may include complementary shapes and positions to maximize the amount of contact when the sections 41, 42 are engaged together.

Figure 7A:
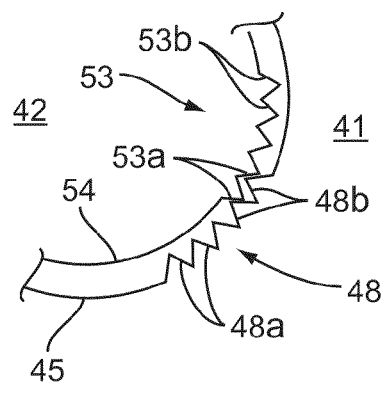
FIGS. 7A and 7B are side schematic view of positions of a first section relative to a second section according to one embodiment.
Figure 7B:
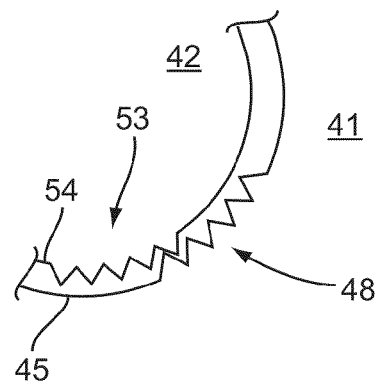

FIGS. 7A-7B illustrate a schematic view of the position of the teeth 48, 53 when the second section 42 is in two different angular positions relative to the first section 41. First section 41 includes teeth 48 each include a first side 48a, and a second side 48b. Second section 42 includes teeth 53 each with a first side 53a, and a second side 53b. The sides 48a, 48b, may be positioned at various angles relative to each other, including an angle of about ninety degrees as illustrated. Sides 53a, 53b, may also be positioned at various angles relative to each other. In one embodiment, the angle formed by teeth 48 matches the angle formed by teeth 53 to increase the contact when the sections 41, 42 are locked together.

FIG. 7A includes the second section 42 positioned at a first angular position relative to the first section 41. A limited number of teeth 53 of the row is engaged with a limited number of teeth 48. In the specific orientation of FIG. 7A, two teeth 48, 53 are engaged together with the surfaces 48a, contacting against surfaces 53a. The remaining teeth 48 are positioned away from teeth 53, such as being positioned in overlap with a non-toothed area of the concave section 45. Likewise, the remaining teeth 53 are positioned away from teeth 48 and may overlap with a non-toothed area of the convex section 54. In one embodiment, FIG. 7A includes an extreme angular position in a first direction of the second section 42.

FIG. 7B includes the second section 42 at a second angular position relative to the first section 42. This may include an extreme angular position in a second direction. One tooth 53 is engaged with one tooth 48. The remaining teeth 53 are positioned in overlap with the non-toothed area of the concave section 45, and remaining teeth 48 are positioned in overlap with the non-toothed area of the convex section 54.

Figure 7C:
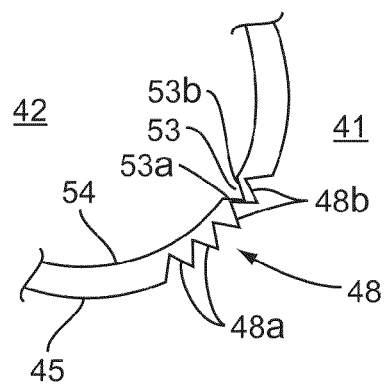
FIGS. 7C and 7D are side schematic view of positions of a first section relative to a second section according to one embodiment.
Figure 7D:
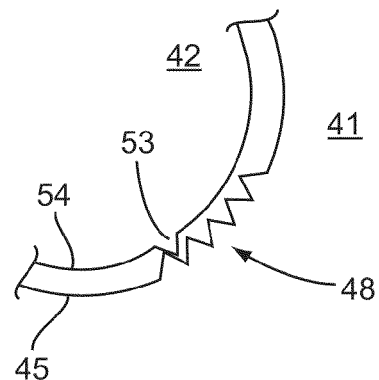

FIGS. 7C and 7D illustrate another embodiment of the first and second sections 41, 42. In this embodiment, the second section 42 includes a single tooth 53 that engage a different tooth 48 along the row of teeth 48. FIG. 7C may include the second section 42 at a first extreme angular position and FIG. 7D may include the second section 42 at an opposite second extreme angular position.

In the various embodiments, there is some overlap with the teeth 48, 53 at the various angular positions. This overlap provides for the teeth 48, 53 to engage together and lock the angular position. The amount of overlap between the teeth 48, 53 may vary depending upon the angular position and orientation and number of teeth 48, 53.

The teeth 48, 53 may be orientated at a variety of different configurations. In embodiments illustrated in FIGS. 5 and 8, the rows are perpendicular to the axis A. This perpendicular positioning provides for some of the teeth 48, 53 to remain in overlap at the various angular positions. The rows of teeth 48, 53 may also be positioned at other alignments relative to the longitudinal axis. Each of rows of teeth 48 and 53 may be arranged in the same positioning (e.g., each row being perpendicular to the axis A), or may be at different positions (e.g., rows of teeth 48 are perpendicular to the axis A and rows of teeth 53 are in non-perpendicular rows).

Figure 8:
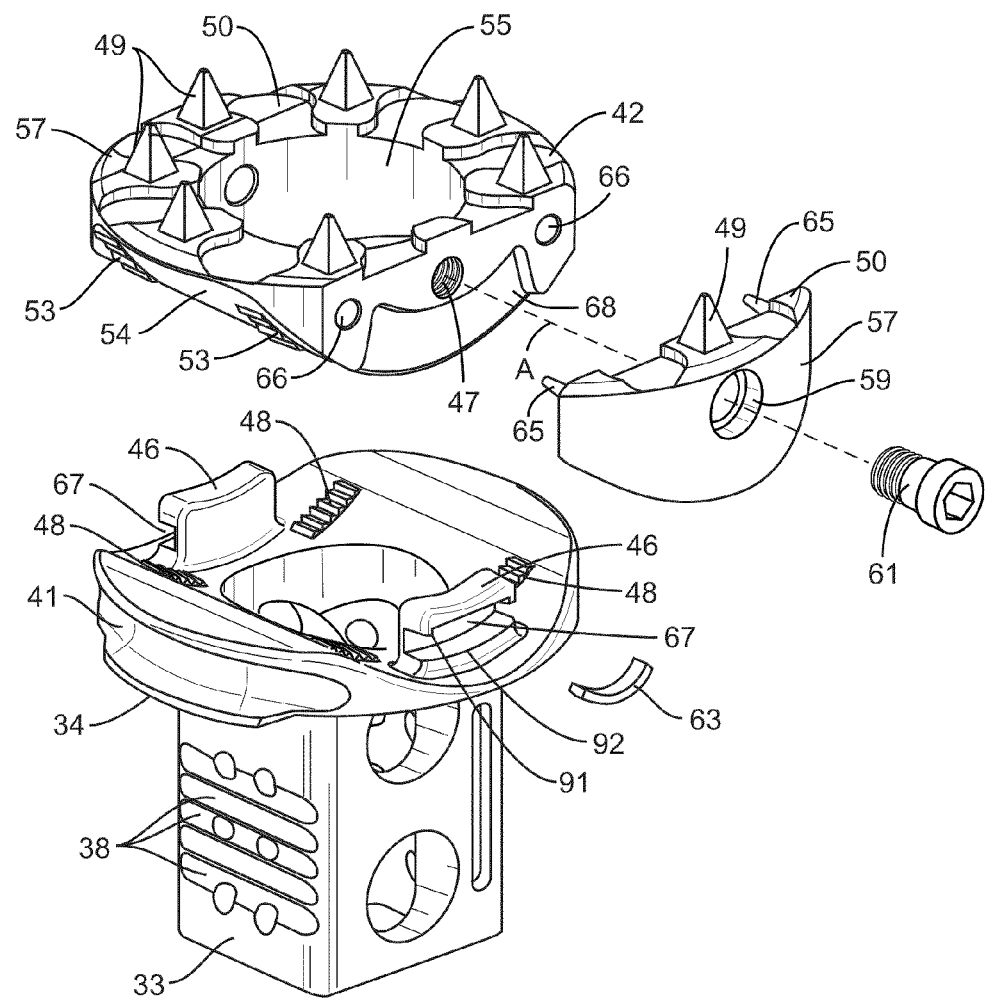
FIG. 8 is an exploded perspective view of an end cap and a section of a body according to one embodiment.

Teeth 48, 53 may also include a variety of different shapes. In one embodiment, teeth 48, 53 are formed as a roughened or knurled surface on the concave and convex sections 45, 54. The surfaces may be on limited portions of the sections 45, 54, or across the entire sections. Teeth 48, 53 may include a variety of shapes, including but not limited to stepped shape as illustrated in FIGS. 5 and 8, rounded outer surfaces, pointed teeth, truncated pointed teeth, and various hybrid configurations of two or more teeth shapes. Further, the spacing between teeth 48, 53 may vary. FIGS. 7A-7D includes the teeth 48, 53 aligned in an end-to-end configuration with the adjacent teeth extending directly together. Teeth 48, 53 may also be spaced apart by gaps of various sizes.

In some embodiments, the sections 41, 42 do not include teeth. These toothless embodiments provide for the second section 42 to be "free floating" to facilitate engagement with a vertebral member at the desired angular position. Once at the desired angular position, a load placed on the implant locks the position of the second section 42. The sections 41, 42 may be maintained at the desired angular positions by contact with the vertebral member 200 when the implant 10 is inserted into the intervertebral space 201. The free floating embodiments may also include roughened surfaces that allow for relatively free movement of the second section 42 under limited loading, and locking under higher loading.

Locking may also be accomplished by one of the sections 41, 42 biting into the opposing section. In these embodiments, the surface of one of the sections 41, 42 is constructed of a harder material than the surface of the opposing section. During loading, the harder material of the one section bites into the softer material of the other section and maintains the angular positioning between the sections 41, 42. The harder material may include teeth or other surface configurations that facilitate the contact and biting with the softer material of the opposing section.

The second section 42 is connected to the first section 41 in various manners. FIG. 5 includes a connection with the fasteners 61 extending through slots 51 in the second section 42 and through the apertures 47 in the posts 46. The slots 51 align with the apertures 47 on the posts 46 when the second section 42 is mounted on the first section 41. The slots 51 are sized to allow the second section 42 to pivot about the fasteners 61. The slots 51 may include curved shapes to allow for the pivoting movement of the second section 42. The curved shape may match or be different than the curvature of the convex section 54. FIG. 6 illustrates a cross sectional view of the second section 42 connected to the first section 41. The fasteners 61 extend through the slots 51 and are threaded to the apertures 47. This connection provides for the second section 42 to pivot.

Figure 9:
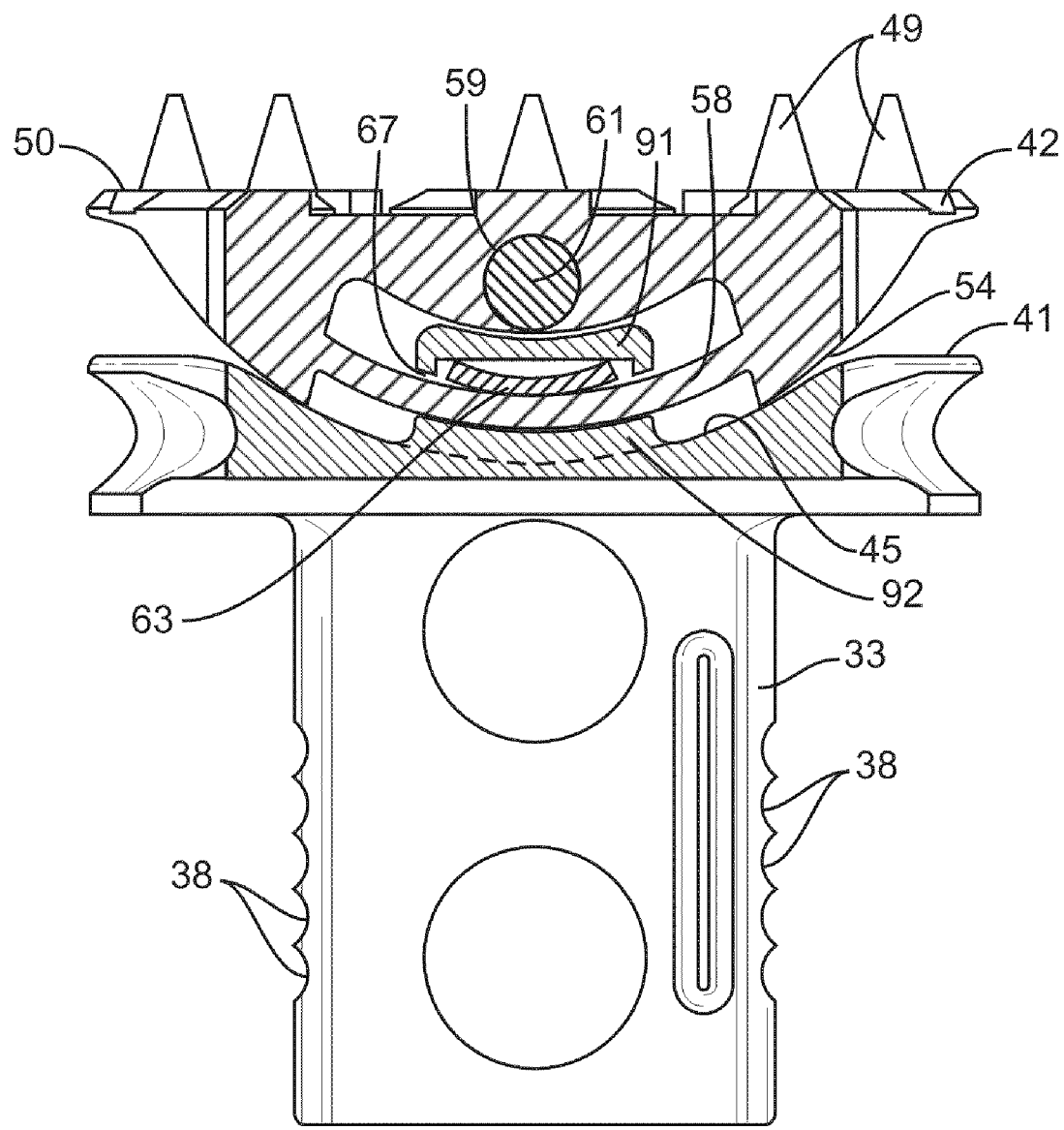
FIG. 9 is a partial sectional view of a first section and a second section connected together according to one embodiment.

FIGS. 8 and 9 illustrate another connection of the first and second sections 41, 42. The outwardly-extending posts 46 include a channel 67 formed between upper and lower extensions 91, 92. The second section 42 includes a main body and a pair of attachments 57. The main body includes recesses 68 positioned on opposing sides and sized to be positioned along the inner sides of the posts 46. The recesses 68 may be wider than the posts 46 to allow for the pivoting movement of the second section 42 relative to the first section 41.

The attachments 57 are sized and shaped to abut against and be connected to the main body. Each of the main body and the attachments 57 may include corresponding surfaces that contact when the attachments 57 are connected to the main body. The main body may further include one or more apertures 66 sized to receive corresponding prongs 65 that extend outward from the attachments 57. Attachments 57 further include an aperture 59 that aligns with the apertures 47 on the main body to receive the fastener 61. As illustrated in FIG. 9, the inner surfaces of the attachments 57 further include a rib 58 that fits within the channels 67 of the posts 46. The ribs 58 slide within the channels 67 during the pivoting movement of the second sections 42. The ribs 58 may include a curved shape that may match the curvature of the convex section 54.

FIG. 8 illustrates one attachment 57 connected to the main body and a second attachment 57 exploded away from the main body. The attachments 57 and corresponding structures of the main body and first section 41 may be substantially the same, or may be different. In one embodiment, the second section 42 includes only one attachment 57. Further, different types of connections may be used to connect the first and second sections 41, 42. By way of example, the connection may include a first post 46 and slot 51 connection as illustrated in FIGS. 5 and 6, and a second rib 58 and channel 67 connection as illustrated in FIGS. 8 and 9. Embodiments may also include a single connection structure between the first and second sections 41, 42. Embodiments may also include more than two connection structures.

The second section 42 may be movably connected to the first section 41. This movement provides for the second section 42 to be spaced away from the first section 41 to disengage the teeth 48, 53 or other locking features and allow for adjusting the angular position of the second section 42. The movement also provides for the second section 42 to move into contact with the first section 41 to engage the teeth 48, 53 or other locking features together and lock the angular position.

One or more biasing members 63 may position the second section 42 relative to the first section 41. The biasing members 63 may include a variety of different shapes and sizes. One type of biasing member 63 includes an elongated leaf spring as illustrated in FIGS. 5-6, and 8-9. The leaf spring includes a curved shape that extends between opposing ends. Biasing members 63 may also include but are not limited to coil springs, flat springs, wave springs, wave washers, Belleville washers, disc washers, torsion springs, and resilient cushioning material such as foam.

The biasing members 63 may force the second section 42 away from the first section 41 for the end cap 40 to float and acquire a particular angular orientation relative to the body 20 during insertion into the intervertebral space 201. Once an axial load is applied, the biasing force is overcome and the angle of the second section 42 is locked. The biasing members 63 may also force the second section 42 into engagement with the first section 41 for the end cap 40 to be preset at a particular angle relative to the body 20. The surgeon presets the angle by overcoming the biasing force, adjusting the angle, then allowing the biasing member or members 63 to bring the sections 41, 42 together to lock the position.

FIGS. 5 and 6 include a pair of biasing members 63 forcing the second section 42 away from the first section 41. Each biasing member 63 is positioned in a space formed between surfaces 71 of the posts 46 and an inner surface 72 of the second section 42. The surfaces 71 are positioned within a recessed section of the posts 46. An outer peripheral wall extends around the surface 72 to maintain the position of the biasing member 63. As best illustrated in FIG. 6, the biasing member 63 contacts against the opposing surfaces 71, 72 when the first and second sections 41, 42 are connected together. The biasing members 63 are configured to apply a force that biases the second section 42 outward away from the first section 41. This causes the teeth 48, 53 to be spaced apart for the second section 42 to pivot prior to insertion of the implant 10 into the intervertebral space. Once implanted, the opposing ends of the implant contact against the vertebral members 200 to overcome the force of the biasing member 63 and move the second section 42 inward towards the first section 41. This inward movement causes the teeth 48, 53 to engage together and lock the angular position of the second section 42 relative to the first section 41 and body 20. Thus, the end cap 40 is configured to accommodate the shape of the vertebral members 200 and the intervertebral space 201.

FIGS. 8 and 9 include the biasing members 63 configured to force the second section 42 towards the first section 41. The biasing member 63 is positioned to contact against the side 91 of the channel 67 and the rib 58 on the attachment 57. The force of the biasing member 63 causes the teeth 48, 53 to lock together to fix the angular position of the second section 42 relative to the first section 41 and body 20. In use, the surgeon selects the desired angular position prior to or during the insertion process. The surgeon is able to overcome the force of the biasing member 63 to set the second section 42 at the desired angular position or drive a particular angular position of the vertebral members 200. Once implanted in the intervertebral space 201, the implant 10 is contacted on opposing sides by the vertebral members 200 to maintain the angular position. The surgeon may also apply a force to second section 42 during the process to overcome the force of the biasing members 63 if the angular position needs to be changed.

The sections 41, 42 may be configured to float angularly relative to each other until the surgeon actively locks the angular position. In one embodiment, each of the sections 41, 42 include multiple apertures. The apertures are positioned for at least one of the apertures of the first section 41 to overlap with at least one of the apertures of the second section 42 at each angular position. The surgeon moves the sections 41, 42 to the desired angular position and then inserts the locking pin through the aligned apertures to lock the sections 41, 42.

These embodiments include a pair of biasing members 63 that apply a force between the sections 41, 42. Various numbers of biasing members 63 may be used in the various embodiments, including a single biasing member 63. Further, different biasing members 63 may be used within the same implant 10. In another embodiment, the implant 10 does not include any biasing members 63. The second section 42 may be positioned at the desired angular position relative to the first section 41 and body 20, and then maintained in that position by contact with the vertebral members 200.

Figure 11:
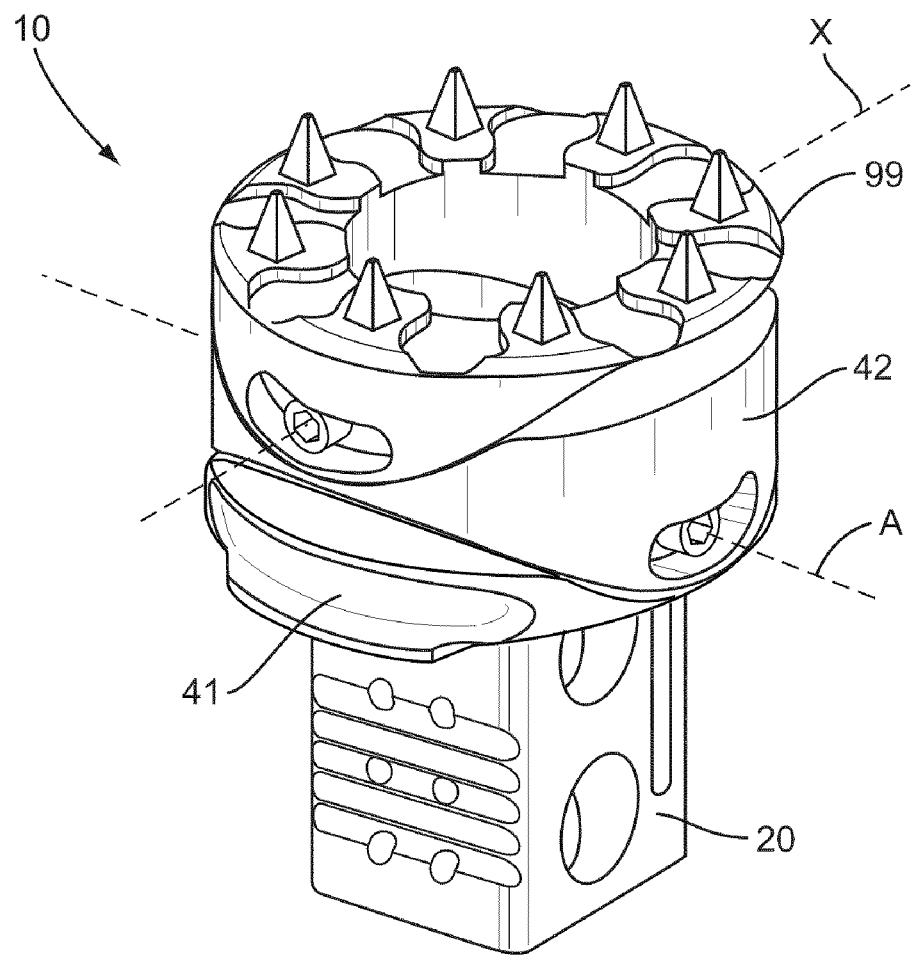
FIG. 11 is a perspective view of an end cap according to one embodiment.

The embodiments described above include mechanisms for the end cap 40 to pivot about a single axis. The end cap 40 may also pivot about one or more additional axes. FIGS. 10 and 11 include the implant 10 with a third section 99 that can pivot about axis X. The implant 10 includes first and second sections 41, 42 that are connected together for pivoting movement. The third section 99 is positioned on an outer surface of the second section 42 and is connected with fasteners 96 that extend through slots 97 on the sidewalls of the third section 99 and into apertures 82 in posts 81 that extend outward from the second section 42. The third section 99 is able to pivot about the longitudinal axis X. The third section 99 may include teeth that engage with teeth on the second section 42 in a manner as explained above between the first and second sections 41, 42. The first, second, and third sections 41, 42, 99 may be positioned at various rotational positions to align the axes A and X as desired. In one embodiment as illustrated in FIG. 11, the axes A, X are perpendicular.

FIG. 12 includes an implant 10 with the first section 41 rotationally attached to the body 20. The first section 41 includes a neck 92 that extends outward and seats within a recess formed between the shelf 37 of the body 20. A lower surface of the first section 41 may further contact against and slide along the support surface 36 of the body 20 during rotational movement. One or more biasing members 63 may be positioned in apertures 35 in the support surface 36 to bias the first section 41 outward from the body 20. This outward positioning may facilitate rotational positioning of the first section 41 and associated longitudinal axis A. The neck 92 may further include a flange that fits within a corresponding recess in the body 20 to connect the first section 41 to the body 20. Further, the biasing members 63 may force balls 69 into contact with the first section 41. The first member 41 may further include a series of detents along an inner surface that are configured to receive the balls. This may provide for a ratcheting movement as the first section 41 is rotated relative to the body 20 and the balls 69 move into and out of the various detents.

In use, the surgeon rotates the first section 41 and connected second section 42 relative to the body 20 to the desired position. The surgeon also pivots the second section 42 to contact against the vertebral member 200. The angular position of the first section 41 relative to the body 20 is set once the implant 10 is inserted into the intervertebral space 201.

Figure 13A:
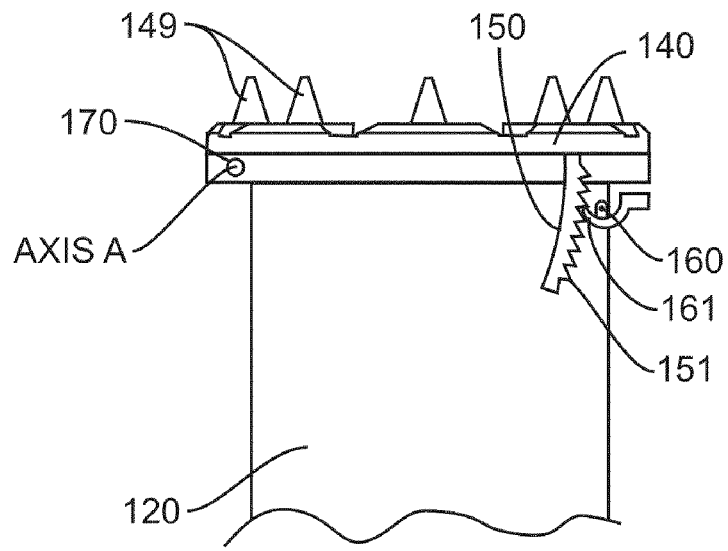
FIG. 13A is a schematic side view of an implant with an end cap in a first orientation according to one embodiment.
Figure 13B:
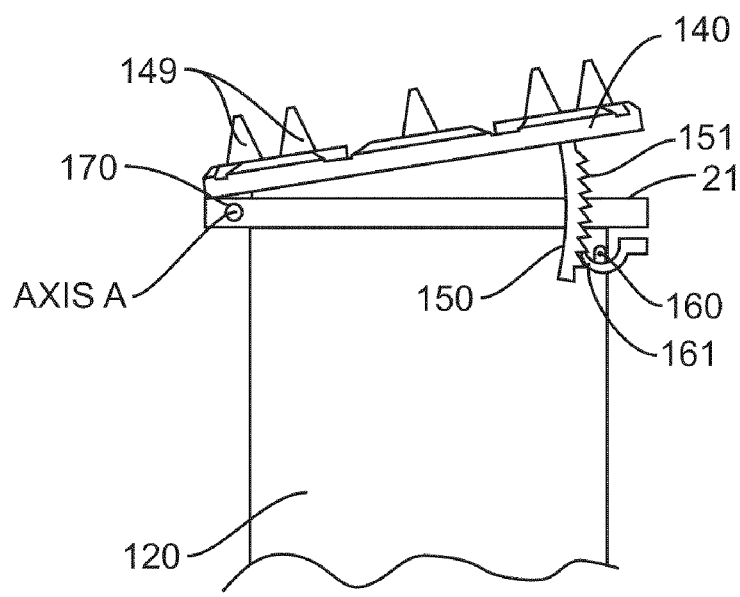
FIG. 13B is a schematic side view of an implant with an end cap in a second orientation according to one embodiment.

FIGS. 13A and 13B include a rack and pawl configuration with the body 120 including a pawl 160 and the end cap 140 including a rack 150. The elements may also be reversed with the end cap 140 including the pawl 160 and the body 120 including the rack 150. The pawl 160 includes a biasing arm with one or more teeth 161. The arm is biased for the one or more teeth 161 to remain in engagement with the rack 150. The rack 150 includes a plurality of teeth 151 along one side that are configured to engage with the pawl 160. The end cap 140 is connected to the body 120 at a pivot 170. The rack and pawl configuration provide for the end cap 140 to be pivoted outward from the body 120 to a desired angular position. The pawl 160 is biased against the rack 150 with the teeth 161 engaging the teeth 151 to maintain the angular position. In one embodiment, the teeth 151, 161 are configured to slide across each other during movement of the end cap 140. The configuration allows for pivoting movement of the end cap 140 in one direction (e.g., away from the body 120), and prevent movement in the opposite direction.

Figure 14A:
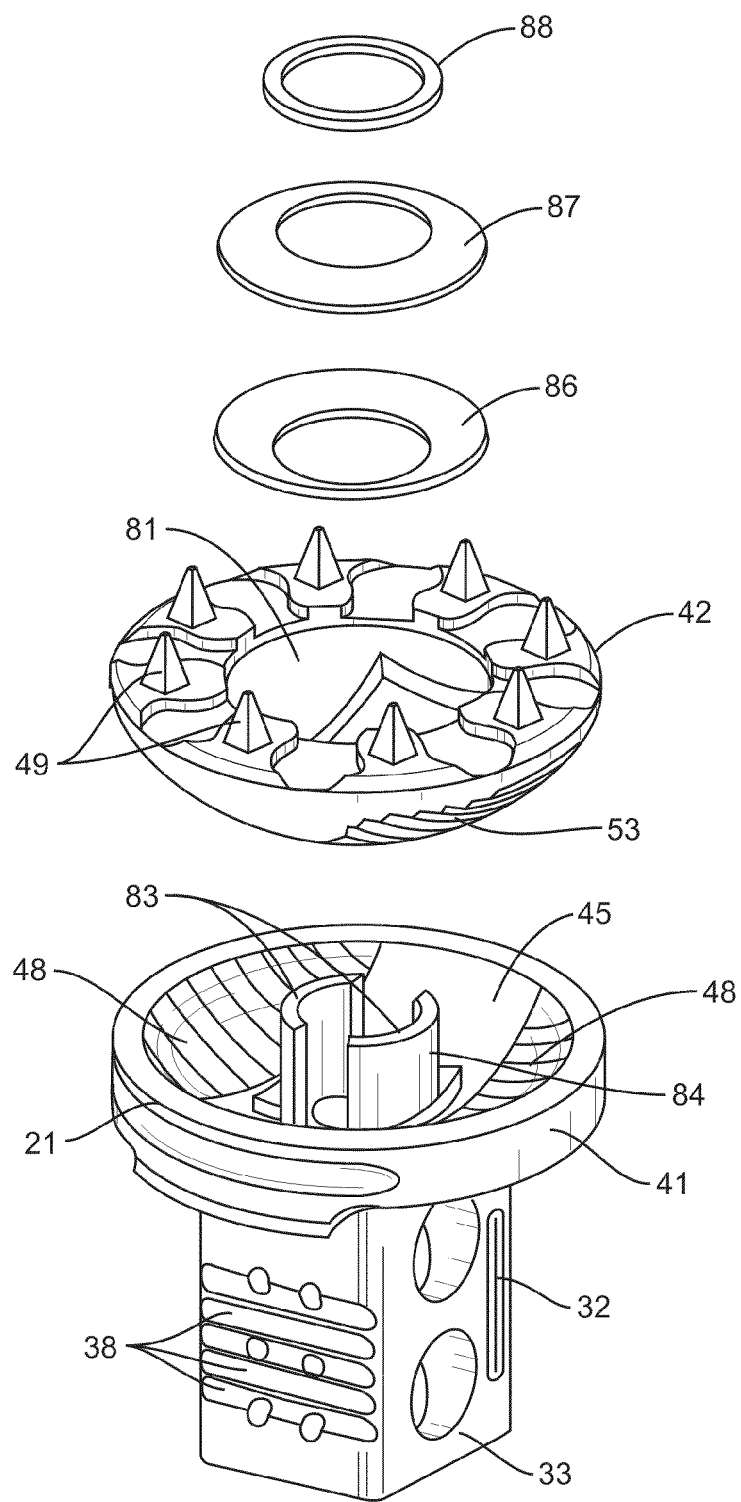
FIG. 14A is an exploded perspective view of an implant according to one embodiment.
Figure 14B:
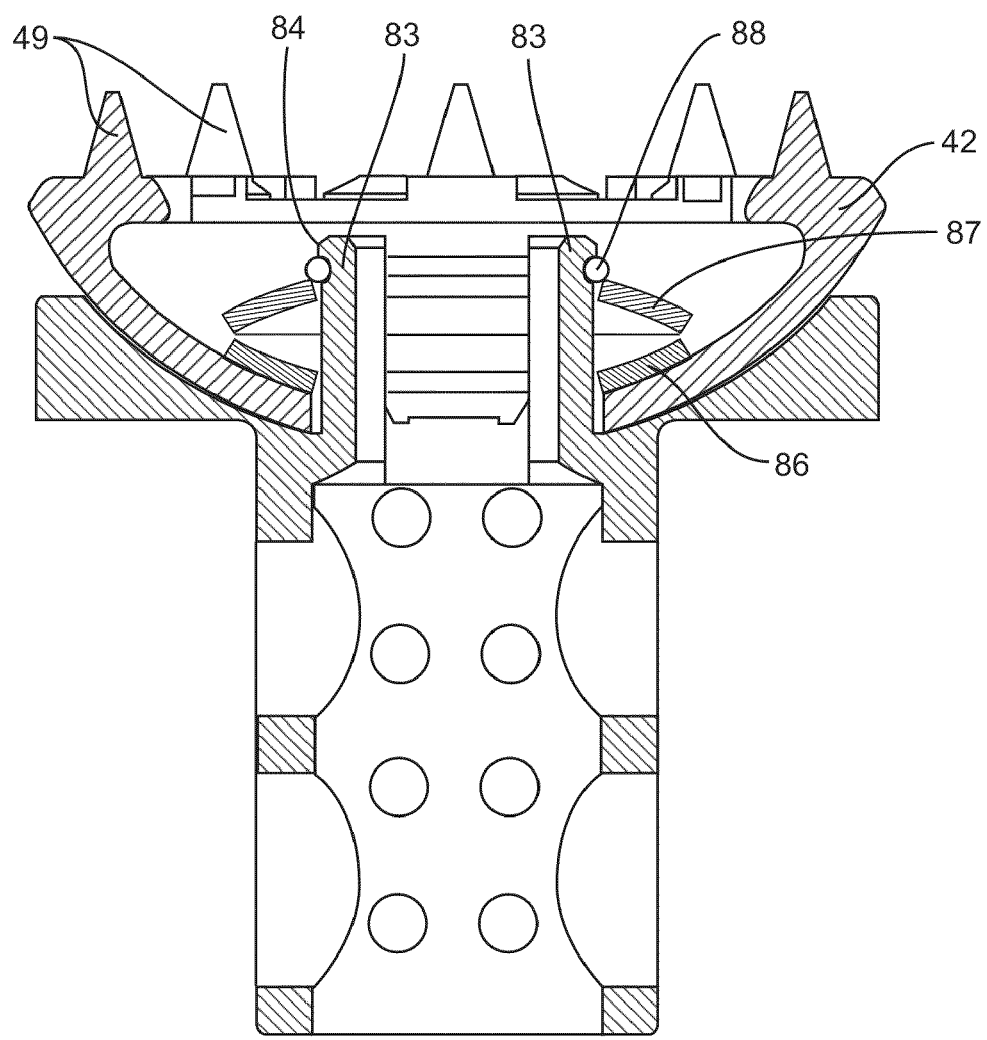
FIG. 14B is a sectional view of an assembled implant of FIG. 14A according to one embodiment.

FIGS. 14A and 14B include an embodiment with the first section 41 including a concave surface that extends into the first end 21. Teeth 48 are positioned about the concave surface. The teeth 48 may cover the entirety or limited sections of the surface. Posts 83 extend outward beyond the concave surface. FIG. 14A includes the posts 83 including circular arcs that complement each other to form a substantially circular construction. Different numbers, sizes, and shapes of posts 83 may also be included. The second section 42 includes a convex lower surface that complements the concave surface of the first section 41. Teeth 53 are positioned on the lower surface to engage with the teeth 48. Teeth 53 may extend outward from the entire lower surface, or limited sections of the lower surface. The second section 42 further includes an aperture 81 sized to extend over the posts 83. Teeth 49 extend outward from the second section 42 to engage with a vertebral member 200.

Opposing washers 86, 87 each include an annular shape sized to fit around the posts 83. The washers 86, 87 include a slight conical shape and provide a biasing force to bias the second section 42 towards the first section 41. As best illustrated in FIG. 14B, washer 86 contacts against an inner surface of the convex lower surface and washer 87 contacts against the posts 83 and the washer 86. In this embodiment, a clip 88 fits under a flange on the posts 83 to maintain the position of the washers 86, 87. In one embodiment, the washers 86, 87 are each Belleville washers. The design may also include other mechanisms instead of the washers 86, 87. Examples includes but are not limited to one or more coil springs, flat springs, wave springs, wave washers, disc washers, torsion springs, and resilient cushioning material such as foam.

In use, the washers 86, 87 apply a biasing force to maintain the teeth 53 of the second section 42 engaged with the teeth 48 of the first section 41. The surgeon can overcome the biasing force and position the second section 42 at the desired angular position relative to the first section 41. The surgeon can release the second section 42 and the biasing force engages the teeth 48, 53 together to lock the angular position. In addition to the angular position being adjustable, the second section 42 may also be rotated about the posts 83 as necessary to facilitate positioning for contact with a vertebral member 200. FIGS. 14A and 14B include a pair of spring washers 86, 87, although embodiments may also include a single spring washer, or three or more spring washers.

Figure 15:
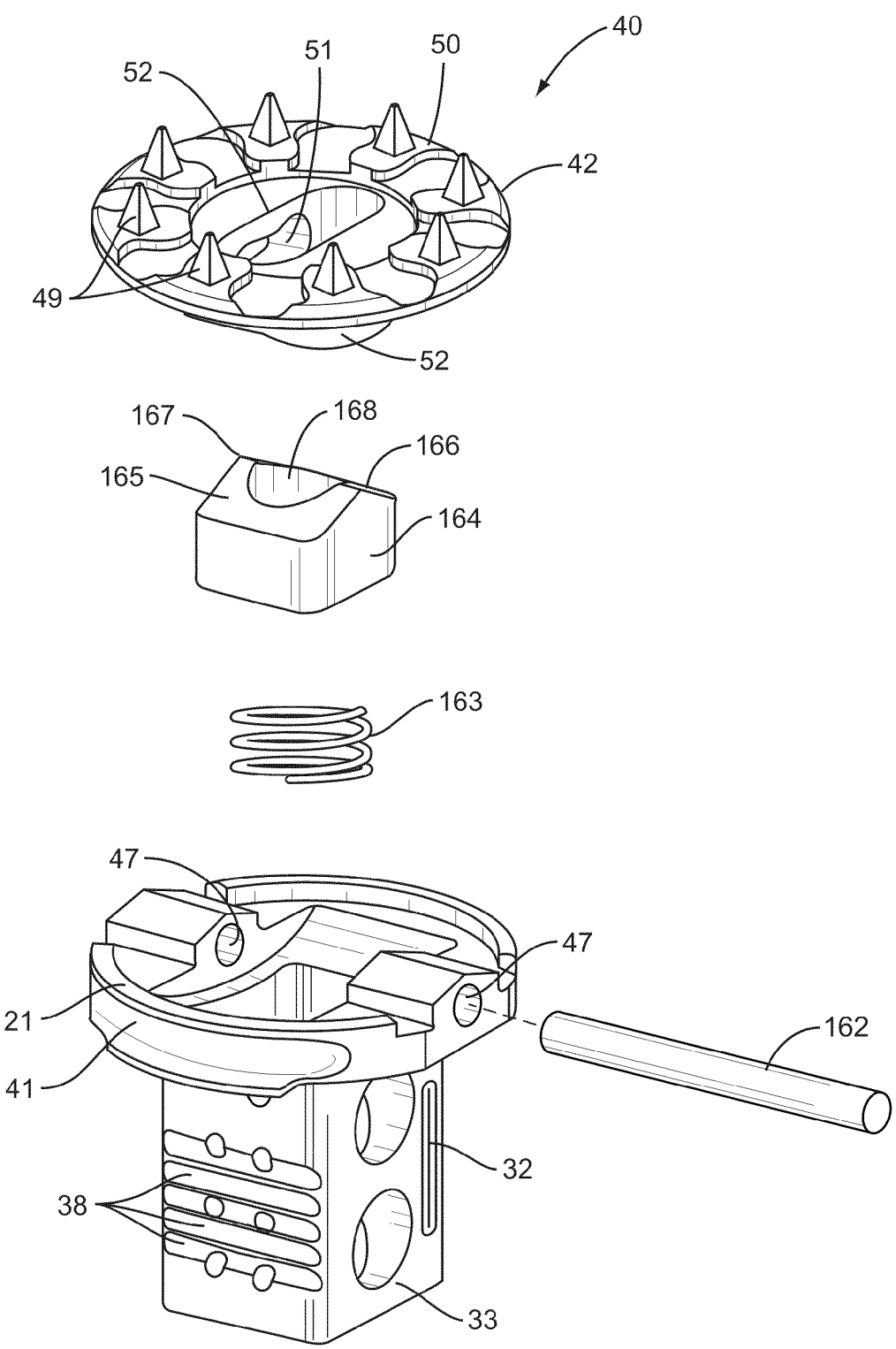
FIG. 15 is an exploded perspective view of an implant according to one embodiment.

FIG. 15 includes a spring-loaded plunger design. A pin 162 extends through apertures 47 in the first section 41. A spring 163 contacts against the pin 162. Spring 163 may include a coil spring as illustrated in FIG. 15, or other structures including but not limited to flat springs, wave springs, wave washers, Belleville washers, disc washers, torsion springs, and resilient cushioning material such as foam. A plunger 164 is positioned on an opposite side of the spring 163 from the first section 41. The plunger 164 includes faces 165, 166 positioned at opposing angles that intersect along an edge 167. In one embodiment, the faces 165, 166 are positioned to form an obtuse angle. In another embodiment, the faces 165, 166 are positioned at a right angle. The second section 42 includes sidewalls 52 with slots 51 sized to receive the pin 162 and attach the second section 42 to the first section 41. An inner surface of the second section 42 may include teeth (not illustrated) configured to contact against the plunger 164.

In use, the spring 163 biases the plunger 164 outward from the first section 41 and into engagement with the teeth on the second section 42. A surgeon can pivot the second section 42 about the pin 162 to adjust the angular position relative to the first section 41. The pivoting movement causes the plunger 164 to move across the teeth in a ratchet-like manner. Once the surgeon selects the desired angular position, the spring 163 maintains the plunger 164 engaged with the teeth to maintain the position.

FIG. 15 includes a single pin 162 that extends across the width and into each of the apertures 47. Pin 162 may also be constructed from multiple sections that may or may not be connected together. In one embodiment, a first pin is positioned in the first aperture 47, and a second pin is positioned in the second aperture 47. The pins are spaced apart and do not extend across or interfere with the hollow interior where bone may grow through the implant.

The implants 10 may include elements from the various embodiments. By way of example, the rotational connection of the first section 41 relative to the body 20 may be included in an implant as illustrated in FIGS. 10 and 11.

Various embodiments include multiple fasteners that connect the sections of the implants together. By way of example, the embodiment of FIGS. 5 and 6 include a pair of fasteners 61 with each fastener 61 sized to extend through one slot 51 and one post 46. The embodiments may also include a single fastener 61 with a length to extend through both slots 51 and posts 46 to connect the first and second sections 41, 42.

In the embodiment described above, the end cap 40 includes first and second sections 41, 42. The end cap 40 may also include a single section. In one embodiment, the body 20 includes a concave section 45, posts 46, and teeth 48 to engage with the end cap 40.

The amount of angular movement of the end cap 40 relative to the body 20 may vary. In one embodiment, the end cap 40 may be able to pivot within a range of about 0-30°.

The implants 10 may include a single pivoting end cap 40 on just one side of the body 20, or may include a second pivoting end cap 40 on a second side of the body 20. In embodiments with multiple end caps 40, the end caps 40 may be the same or different, and may include for the same or different directions for pivoting.

The end caps 40 may be integral to the body 20, or may be a separate component that the surgeon attaches to the body 20. The surgeon may attach the end caps 40 prior to insertion into a patient, or after the body 20 and end cap 40 have been inserted into the patient.

Many of the designs include an interior section having a concave surface that receives a convex surface of an outer member. By way of example, FIG. 5 includes a concave section 45 on the interior first section 41 and a convex section 54 on the exterior second section 42. This arrangement may be switched with the interior section having a convex surface and the exterior section having a concave surface. Using the example of FIG. 5, this would include the first section 41 including a convex surface that extends outward from and engages with a concave surface in the second section 42. The arrangement of concave-convex surfaces may vary in the various embodiments.

The implants 10 may be implanted within a living patient for the treatment of various spinal disorders. The implant 10 may also be implanted in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An implant for insertion into an intervertebral space between first and second vertebral members, the implant comprising:
    a body with opposing first and second sides, the first side including a first locking feature;
    an end cap connected to the body and including a first side with a contact surface that faces away from the body and configured to contact against one of the first and second vertebral members when the implant is positioned in the intervertebral space, the end cap also including a second side that faces towards the body and includes a second locking feature;
    a connection mechanism that connects the end cap and the body and forms a single rotational axis perpendicular to a longitudinal axis of the body for the end cap to pivot to various angular positions relative to the body;
    the first locking feature and the second locking feature configured to engage together and maintain the angular position of the end cap relative to the body when the implant is positioned in the intervertebral space; and
    a resilient biasing member that engages the body and the end cap to position the end cap relative to the body, said biasing member engaging the body and the end cap to bias the body away from the end cap and the first locking feature away from the second locking feature or bias the body towards the end cap and the first locking feature towards the second locking feature.

2. The implant of claim 1, wherein the first locking feature includes a first tooth set and the second locking feature includes a second tooth set, each of the first and second tooth sets including at least one tooth.

3. The implant of claim 2, wherein each of the first and second tooth sets are in an overlapping position at each of the angular positions.

4. The implant of claim 1, wherein the connection mechanism is configured for the end cap to move towards and away from the body between a first position with the first and second locking features spaced apart to adjust the angular position of the end cap relative to the body, and a second position with the first and second locking features engaged together to lock the angular position.

5. The implant of claim 1, wherein the body includes an outwardly extending post with a first aperture and the end cap includes a second aperture through a sidewall, the connection mechanism including a fastener that extends through the first and second apertures to connect the end cap and the body.

6. The implant of claim 1, further comprising a second end cap connected to the second end of the body, the second end cap being movable to adjust an angular position of the second end cap relative to the body about a different axis that is perpendicular to the longitudinal axis of the body.

7. The implant of claim 1, wherein the end cap is rotationally adjustable relative to the body about the longitudinal axis of the body.

8. The implant of claim 1, wherein the first locking feature is constructed from a first material and the second locking feature is constructed from a second material, the first and second materials including different hardnesses.

9. The implant of claim 1, wherein the end cap is modularly attached to the body.

10. An implant for insertion into an intervertebral space between first and second vertebral members, the implant comprising:
    a body with a first side and a second side;
    a platform positioned at the first side of the body and including a receiving side that faces away from the body, the receiving side including a first locking feature;
    an end cap connected to the platform and including a first side with a contact surface configured to contact against one of the first and second vertebral members when the implant is positioned in the intervertebral space, and a second side that faces towards the platform and includes a second locking feature;
    a connection mechanism that connects the end cap and the body and is configured for the end cap to pivot about a pivot axis to a range of angular positions relative to the body;
    a resilient biasing member that contacts against the end cap to position the end cap relative to the platform along a longitudinal axis of the implant, said resilient biasing member engaging the platform and the end cap to bias the platform away from the end cap and the first locking feature away from the second locking feature or bias the platform towards the end cap and the first locking feature towards the second locking feature;
    the first and second locking features being shaped and configured to engage together and maintain the angular position of the end cap relative to the body when the implant is positioned in the intervertebral space.

11. The implant of claim 10, wherein each of the first and second locking features include at least one tooth.

12. The implant of claim 10, wherein the pivot axis is perpendicular to the longitudinal axis of the body.

13. The implant of claim 10, wherein the connection mechanism is configured to limit pivoting movement between the end cap and the platform to a single plane.

14. The implant of claim 10, wherein the end cap is rotatably connected to the body to rotate about the longitudinal axis of the implant.

15. The implant of claim 10, wherein the platform includes a concave shape and the end cap includes a convex shape that extends into the concave shape of the platform during pivoting movement of the end cap relative to the platform.

16. The implant of claim 10, wherein the platform includes a convex shape and the end cap includes a concave shape, the convex shape of the platform extends into the concave shape of the end cap during pivoting movement of the end cap relative to the platform.

17. The implant of claim 10, wherein the end cap includes first and second sections that are connected together at a second pivot axis.

\* \* \* \* \*